(12) United States Patent
Lupton et al.

(10) Patent No.: US 8,133,243 B2
(45) Date of Patent: Mar. 13, 2012

(54) DEVICE FOR UNBLOCKING AN OCCLUDED VESSEL, AND A METHOD FOR UNBLOCKING AN OCCLUDED VESSEL

(76) Inventors: Henry William Lupton, Oranmore (IE); Leonard Melvyn Shapiro, Coton (GB)

( * ) Notice: Subject to any disclaimer, the term of this patent is extended or adjusted under 35 U.S.C. 154(b) by 240 days.

(21) Appl. No.: 12/414,077

(22) Filed: Mar. 30, 2009

(65) Prior Publication Data

US 2009/0306597 A1 Dec. 10, 2009

(30) Foreign Application Priority Data

Mar. 28, 2008 (IE) .................................. S2008/0226

(51) Int. Cl.
*A61B 17/22* (2006.01)
(52) U.S. Cl. ........................................................ 606/159
(58) Field of Classification Search .................. 604/104; 606/127, 128, 159, 160, 191–195, 198
See application file for complete search history.

(56) References Cited

U.S. PATENT DOCUMENTS

| | | | |
|---|---|---|---|
| 4,445,509 A | 5/1984 | Auth | |
| 4,653,496 A | 3/1987 | Bundy et al. | |
| 4,732,154 A | 3/1988 | Shiber | |
| 5,078,723 A | 1/1992 | Dance et al. | |
| 5,304,199 A | 4/1994 | Myers | |
| 5,345,937 A | 9/1994 | Middleman et al. | |
| 5,409,470 A * | 4/1995 | McIntyre et al. | 604/528 |
| 6,235,000 B1 | 5/2001 | Milo et al. | |
| 6,533,753 B1 * | 3/2003 | Haarstad et al. | 604/96.01 |
| 6,579,302 B2 | 6/2003 | Duerig et al. | |
| 6,605,062 B1 | 8/2003 | Hurley et al. | |
| 6,629,987 B1 | 10/2003 | Gambale et al. | |
| 7,306,617 B2 | 12/2007 | Majercak | |
| 2004/0073243 A1 * | 4/2004 | Sepetka et al. | 606/159 |
| 2004/0230219 A1 | 11/2004 | Roucher, Jr. | |
| 2006/0184186 A1 * | 8/2006 | Noone | 606/159 |
| 2007/0265563 A1 | 11/2007 | Heuser | |
| 2007/0288036 A1 | 12/2007 | Seshadri et al. | |

* cited by examiner

*Primary Examiner* — Ryan Severson
(74) *Attorney, Agent, or Firm* — Sughrue Mion, PLLC

(57) ABSTRACT

A device for unblocking an occlusion (3) in an occluded vessel (2) comprises a catheter (5) having an inflatable balloon (19) located at a distal leading end (8) thereof so that by inflating the balloon (19) the leading end of the catheter (5) may be anchored in the occluded vessel (2) or in a vessel adjacent the occluded vessel (2) with the leading end adjacent the occlusion (3). A guide wire (12) terminating in a pointed distal tip (18) is urgeable through a bore (10) in the catheter (5) for engaging and penetrating through the occlusion (3). A leading portion (17) of the guide wire (12) is externally threaded at (26), and is engageable with an internally threaded portion (25) of the bore (10) adjacent a leading portion (9) of the catheter (5), so that when the catheter (5) is anchored by the balloon (19) with the leading portion (9) of the catheter (5) adjacent and abutting the occlusion (3) with the external threads (26) of the guide wire (12) engaging the internal threads (25) of the catheter (5), rotation of the guide wire (12) urges the distal tip (18) of the guide wire (12) into engagement with the occlusion (3) and to penetrate through the occlusion (3).

19 Claims, 4 Drawing Sheets

Figure 1:
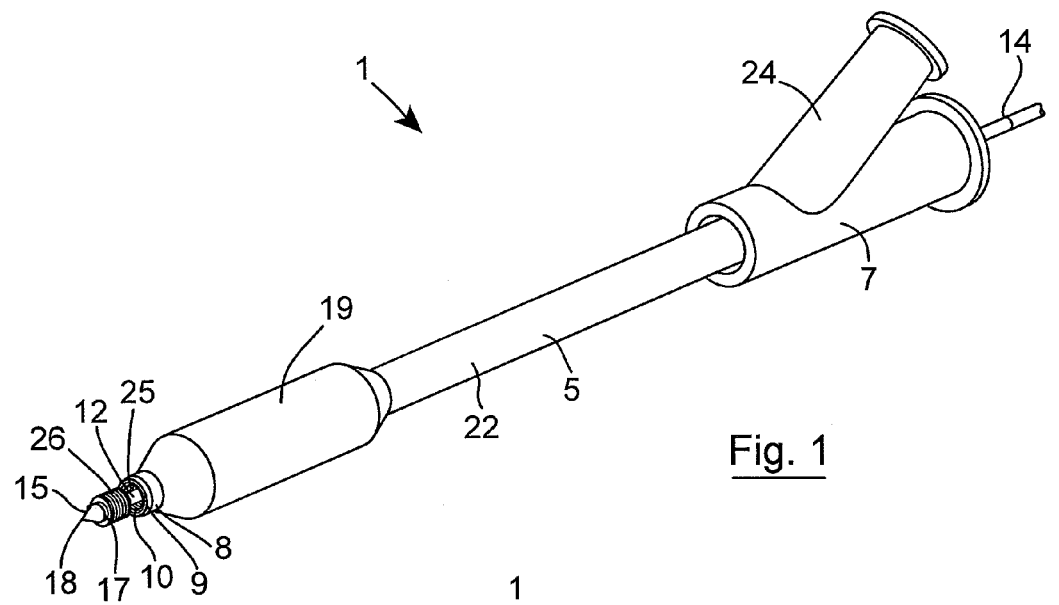

DEVICE FOR UNBLOCKING AN OCCLUDED VESSEL, AND A METHOD FOR UNBLOCKING AN OCCLUDED VESSEL

The present invention relates to a device for unblocking an occluded vessel, for example, unblocking an occluded vessel in a human or animal subject, and in particular, though not limited to a device for unblocking an occluded blood vessel, for example, a vessel in the cardiovascular system, and the invention also relates to a method for unblocking a vessel, for example, unblocking a vessel in a human or animal subject, and in particular, though not limited to a method for unblocking an occluded vessel, such as an occluded blood vessel of the type in the cardiovascular system. The invention also relates to a device and a method for remotely forming one of an opening and a bore through one of a medium within a vessel, a medium separating two vessels and a medium forming a vessel.

Occlusion of blood vessels results from a variety of tissue growth within the vessel. The tissue can become dense and fibrous, and its surface can calcify and harden. The most common minimally invasive treatment for unblocking such vessels is a treatment which is referred to as angioplasty. In an angioplasty treatment a balloon catheter is inserted into the arterial or venal system, typically through one of the femoral arteries or the radial arteries, and is passed through the arterial or venal system to the occluded site. The balloon catheter terminates in a leading portion which carries a balloon, and the leading portion is urged through the occlusion so that the balloon in a deflated state is positioned in the occlusion. Inflating of the balloon dilates the occluded vessel, and a stent, which typically is of tubular wire mesh construction is carried on the exterior of the balloon and is expanded by the inflating of the balloon. The expanded stent remains in place in the occluded region after deflation of the balloon. The stent acts as an implanted scaffold within the vessel for maintaining the occluded region of the vessel dilated.

However, in order to carry out an angioplasty treatment, the blockage must first be traversed by a wire, typically, a guide wire, which acts as a rail over which the balloon catheter is advanced to the occlusion. Failure to cross the occlusion with the guide wire or to position the balloon catheter with the balloon located within the occlusion requires reverting to traditional surgical invasive techniques in order to unblock the occlusion.

Typically, in an angioplasty treatment the guide wire which is advanced to the occluded vessel is a relatively stiff wire, and where the occlusion is relatively soft, manually urging the guide wire in its axial direction is sufficient to urge the guide wire through the occlusion. However, in cases where the occlusion becomes calcified and hardened, it is necessary to employ a laser catheter or a radio frequency guide wire in an attempt to pass through the occlusion. Such laser catheters and radio frequency guide wires require relatively expensive external power packs, and also require highly trained personnel for their operation. Additionally, known minimally invasive systems for unblocking an occlusion must be controlled externally of the body by pushing the guide wire through a catheter, which may or may not be a balloon catheter. Thus, control of the tip of the guide wire which is being urged through the occlusion is arbitrary, and there is no guarantee that the tip of the guide wire remains in a substantially central position within the vessel as it is being advanced into engagement with the occlusion. Indeed, it is not uncommon for a guide wire as it is being advanced into engagement with an occlusion, and in particular a relatively hard occlusion, to slide to one side of the occlusion, and thus, lead to dissection of the blood vessel where the tip of the guide wire passes through the wall of the blood vessel, thus separating an inner lining of the wall of the blood vessel from the outer lining. This can create a false lumen within the wall of a blood vessel. In extreme cases the guide wire on slipping to the side of the occlusion, may extend through and exit the wall of the blood vessel, thus perforating the blood vessel, which results in internal bleeding. This problem is further compounded when the occluded vessel is within the cardiovascular system, since the heart moves as it beats, and thus, it is virtually impossible to maintain the tip of the guide wire centrally in the occluded vessel.

Accordingly, there is a need for a device and a method for minimally invasively unblocking an occluded blood vessel which addresses the problems of known devices and methods.

The present invention is directed towards providing a device and a method for minimally invasively unblocking an occluded vessel at a remote site, for example, though not limited to an occluded blood vessel in a human or animal subject. The invention also relates to a method and a device for forming one of an opening and a bore through one of a medium within a vessel, a medium separating two vessels and a medium forming a vessel.

According to the invention there is provided a device for unblocking an occluded vessel at a remote site having an occlusion therein, the device comprising a first elongated member for passing through a lumen to the occluded vessel, the first member terminating in a distal leading portion, the leading portion having a bore extending axially therethrough, an anchoring means located on the first member for anchoring the first member with the leading portion thereof adjacent the occlusion, and a second elongated member terminating in a distal leading portion urgeable through the bore in the leading portion of the first member, the leading portion of the second member terminating in a distal tip for urging through the occlusion for unblocking the occluded vessel, the second member being co-operable with the first member so that the second member is urgeable off the anchored first member into engagement with the occlusion.

Preferably, a means is provided for converting rotational motion of the second member relative to the first member into linear motion of the second member for advancing the second member into engagement with the occlusion.

In one embodiment of the invention the bore of the leading portion of the first member is internally threaded, and the leading portion of the second member is externally threaded for co-operating with the threaded bore of the first member for advancing the leading portion of the second member into engagement with the occlusion.

Preferably, the anchoring means is located adjacent the leading portion of the first member.

Advantageously, the anchoring means comprises an inflatable balloon located on the first member.

In one aspect of the invention the leading portion of the first member extends through the inflatable balloon so that the inflatable balloon defines with the leading portion of the first member an annular hollow interior region. Preferably, the inflatable balloon is remotely inflatable. Advantageously, the first member comprises a communicating means for accommodating an inflating medium for remotely inflating the inflatable balloon.

In another aspect of the invention the bore in the leading portion of the first member extends through the first member to a proximal end thereof for accommodating the second member therethrough.

Preferably, the first member comprises an elongated catheter, and the second member comprises an elongated wire of relatively high torsional rigidity for transferring angular rotation of the second member adjacent a proximal end thereof into angular rotation adjacent the distal end thereof.

Advantageously, the anchoring means is adapted for engaging the wall of one of the occluded vessel and a vessel adjacent the occluded vessel for anchoring the leading portion of the first member adjacent the occlusion.

In one aspect of the invention the device is adapted for unblocking an occluded vessel in a human or animal subject.

In another aspect of the invention the vessel is a blood vessel.

Additionally, the invention provides a method for unblocking an occluded vessel at a remote site having an occlusion therein, the method comprising urging a first elongated member through a lumen for locating a distal leading portion of the first member adjacent the occlusion, anchoring the first member by an anchoring means with the leading portion of the first member adjacent the occlusion, locating a distal leading end of an elongated second member in a bore extending through the leading end of the first member to co-operate with the first member, and urging the second member off the anchored first member for urging a distal tip of the leading portion of the second member into engagement with the occlusion.

Preferably, the distal tip of the second member is urged into engagement with the occlusion by locating the second member relative to the first member, rotating the second member relative to the first member, and converting the rotational motion of the second member into linear motion of the second member relative to the first member.

In one embodiment of the invention an external thread on the leading portion of the second member is engaged with an internal thread in the bore of the first member for converting the rotational motion of the second member relative to the first member into the linear motion of the second member relative to the first member.

Advantageously, the second member extends through a bore in the first member which extends from the bore in the leading portion of the first member to a proximal end of the first member.

In one aspect of the invention the first member is anchored by engaging the anchoring means with a wall of one of the occluded vessel and a vessel adjacent the occluded vessel.

In another aspect of the invention the anchoring means comprises an inflatable balloon located on the first member, and the inflatable balloon is inflated for anchoring the first member with the leading portion thereof adjacent the occlusion.

In one aspect of the invention the method is adapted for unblocking an occluded vessel in a human or animal subject.

In another aspect of the invention the vessel is a blood vessel.

In another embodiment of the invention the first member with the second member engaged in the occlusion is withdrawn through the lumen, and a balloon stent catheter with a stent located on a balloon of the balloon stent catheter is passed through the lumen over the second member until the balloon with the stent thereon is located in the occlusion, and the balloon of the balloon stent catheter is inflated for dilating the occlusion. Preferably, the balloon of the balloon stent catheter is deflated and the balloon stent catheter and the second member are withdrawn through the lumen leaving the stent in place in the occlusion.

The invention also provides a device for remotely forming one of an opening and a bore through one of a medium within a vessel, a medium separating two vessels and a medium forming a vessel, the device comprising a first elongated member for passing through a lumen to the medium, the first member terminating in a distal leading portion, the distal leading portion having a bore extending axially therethrough, an anchoring means being located on the first member for anchoring the first member with the leading portion thereof adjacent the medium, a second elongated member terminating in a distal leading portion urgeable through the bore in the leading portion of the first member, the leading portion of the second member terminating in a distal tip for urging through the medium to form the one of the opening and the bore therethrough, the second member being co-operable with the first member so that the second member is urgeable off the anchored first member into engagement with the medium.

The invention further provides a method for remotely forming one of an opening and a bore through one of a medium within a vessel, a medium separating two vessels and a medium forming a vessel, the method comprising urging a first elongated member through a lumen for locating a distal leading portion of the first member adjacent the medium, anchoring the first member by an anchoring means with the leading portion of the first member adjacent the medium, locating a distal leading end of an elongated second member in a bore extending through the leading end of the first member to co-operate with the first member, urging the second member off the anchored first member for urging a distal tip of the leading portion of the second member into engagement with the membrane.

The advantages of the invention are many. A particularly important advantage of the invention is that it facilitates axial alignment of the distal tip of the second member with an occlusion in a vessel, and furthermore, facilitates penetrating of the occlusion by the distal tip of the second member substantially along the central axis of the vessel. A further advantage of the invention is that the distal leading portion of the second member is urgeable into and through the occlusion off the leading portion of the first member, since the first member is anchored in or adjacent the occluded vessel. In other words, the anchoring of the first member in or adjacent the occluded vessel provides a solid anchorage against which the second member is urgeable into and through the occlusion.

Similar advantages are obtained from the invention when the device and the method are used for forming an opening or a bore through a medium which may be located in a vessel, separating a pair of vessels or forming a vessel.

Figure 2:
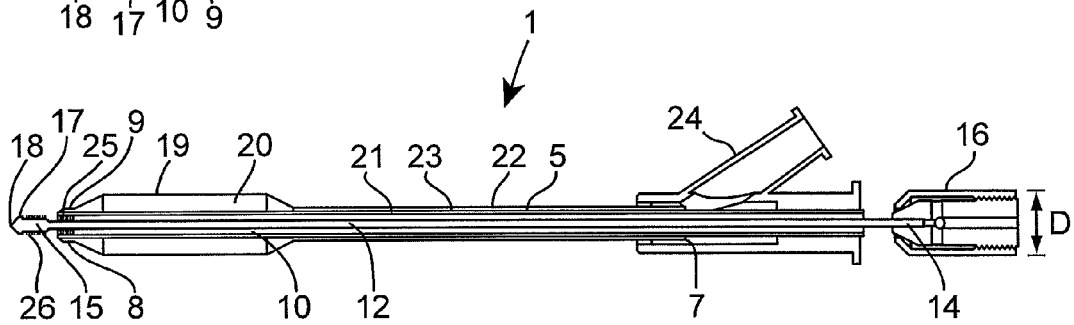
Figure 3:
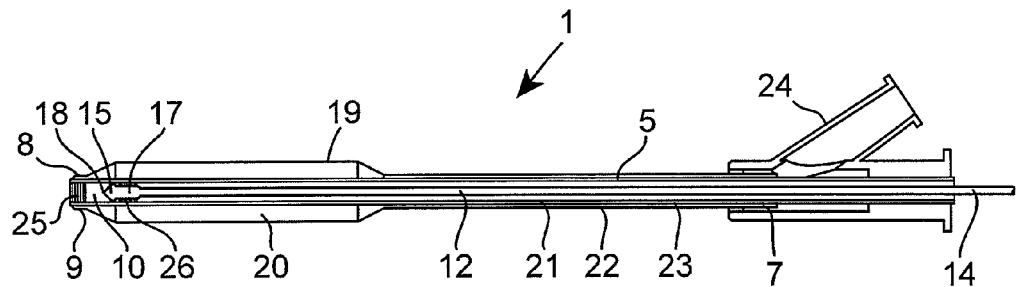
Figure 4:
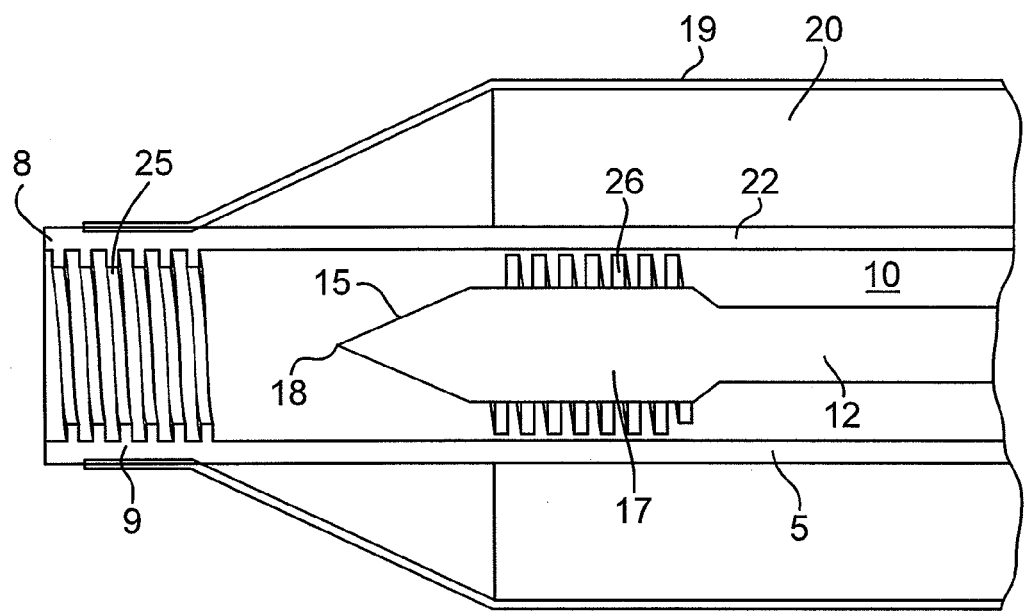
Figure 5:
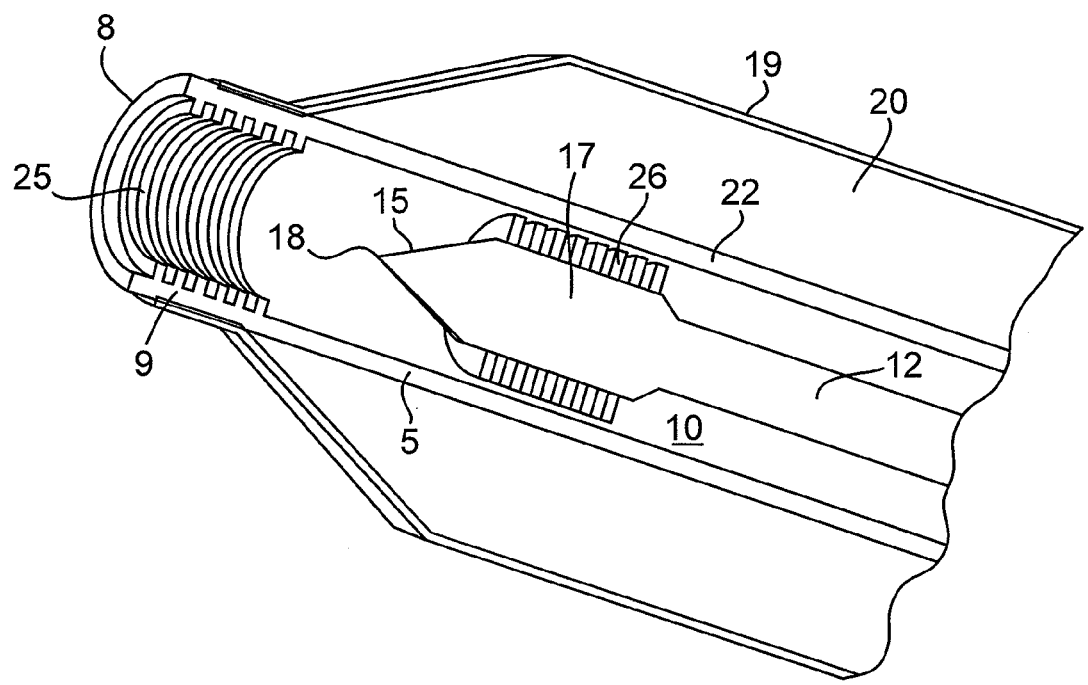
Figure 6:
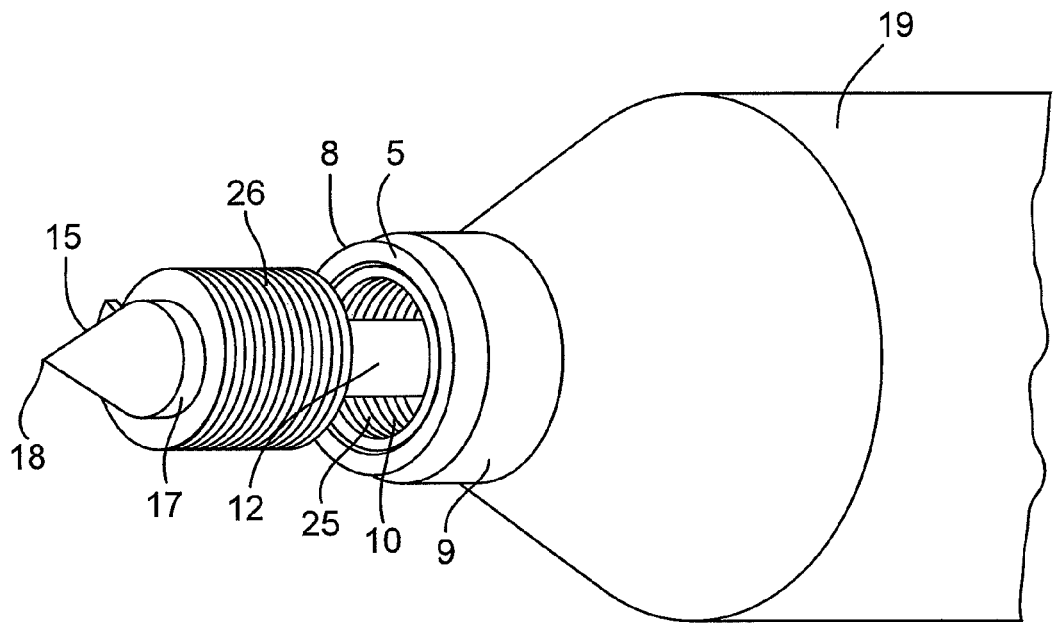
Figure 7:
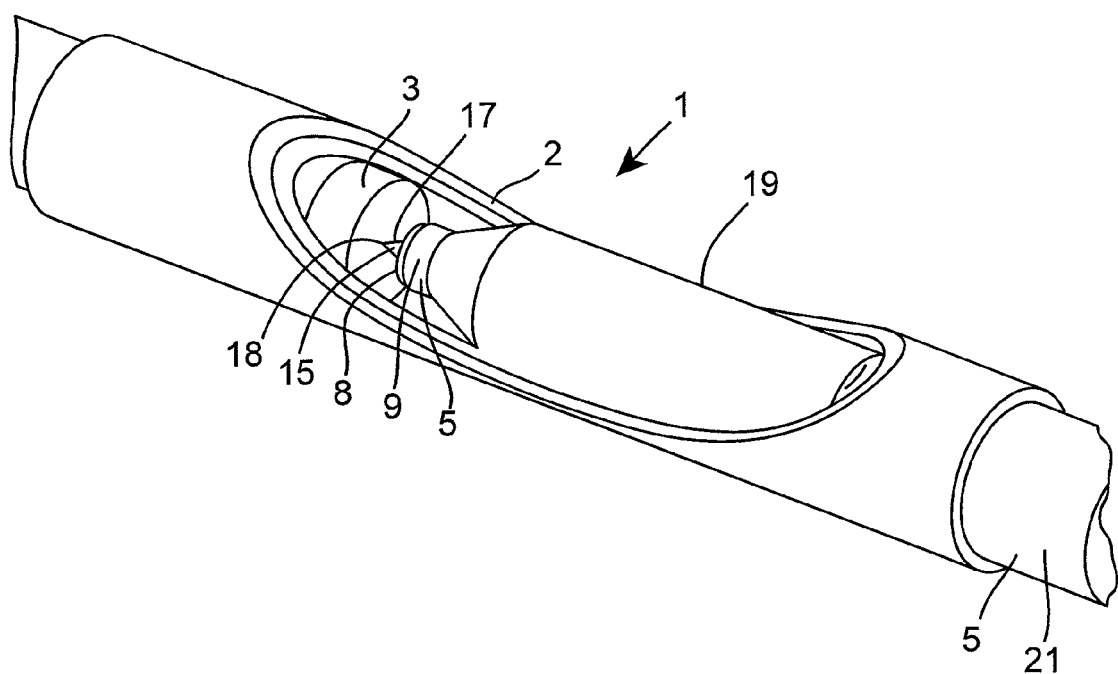
Figure 8:
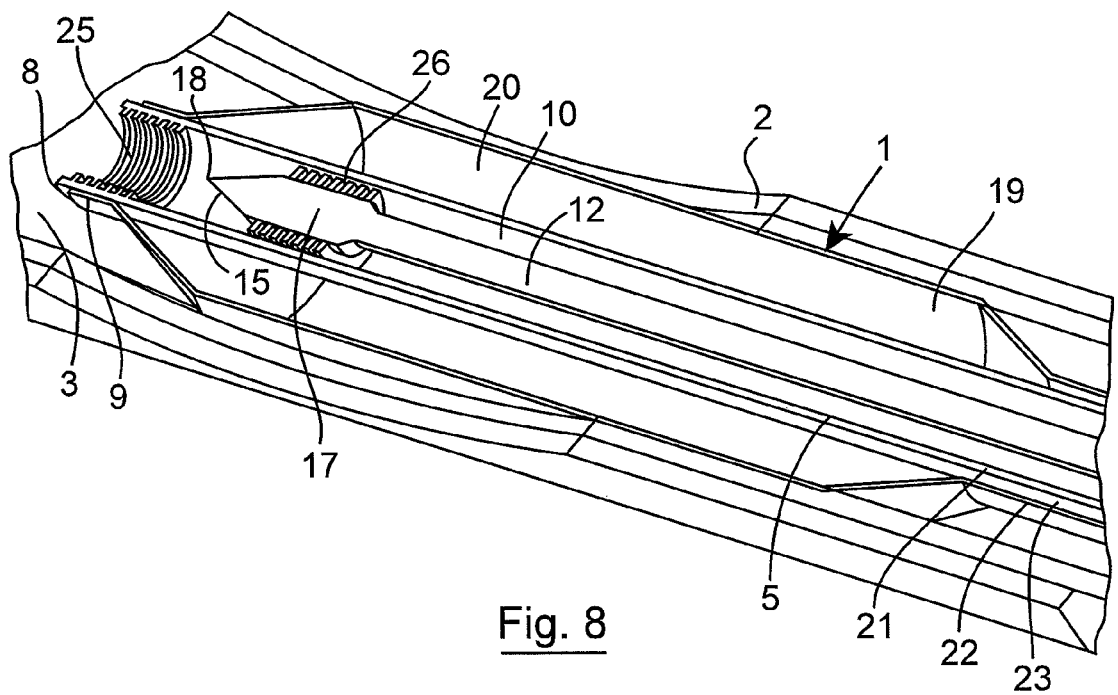
Figure 9:
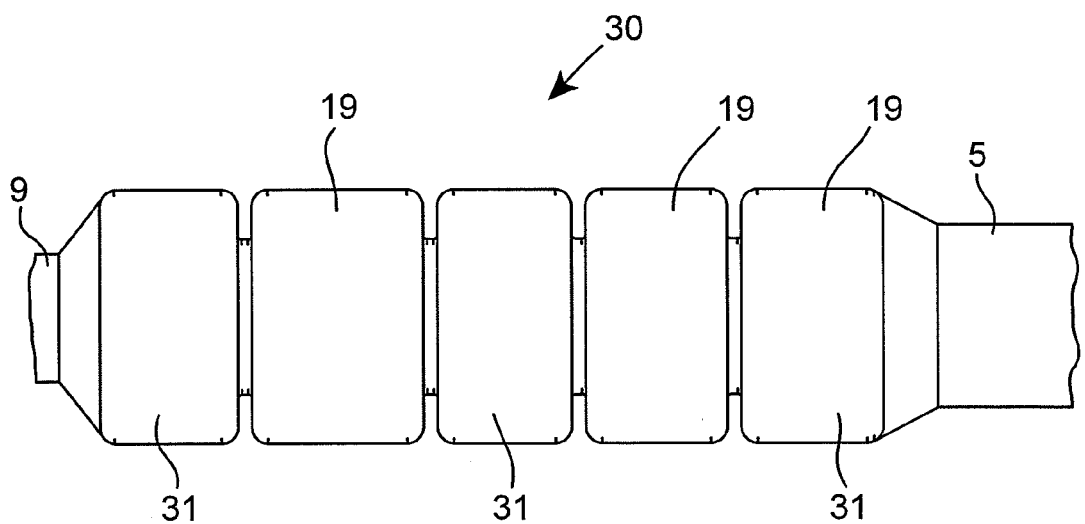

The invention will be more clearly understood from the following description of some preferred embodiments thereof, which are given by way of example only, with reference to the accompanying drawings, in which:

FIG. 1 is a perspective view of a device according to the invention for unblocking an occluded vessel, FIG. 2 is a cross-sectional side elevational view of the device of FIG. 1, FIG. 3 is a cross-sectional side elevational view of the device of FIG. 1 showing a portion of the device in a different position, FIG. 4 is an enlarged cross-sectional side elevational view of a portion of the device of FIG. 1, FIG. 5 is an enlarged perspective cross-sectional view of the portion of FIG. 4 of the device of FIG. 1, FIG. 6 is an enlarged perspective view of the portion of FIG. 4 of the device of FIG. 1, FIG. 7 is a cutaway perspective view of the device of FIG. 1 in use, FIG. 8 is a perspective cross-sectional view of the device of FIG. 1 also in use, and FIG. 9 is an enlarged side elevational view of a portion of a device according to another embodiment of the invention for unblocking an occluded vessel.

Referring to the drawings, and initially to FIGS. 1 to 8 thereof, there is illustrated a device according to the invention, indicated generally by the reference numeral 1, for unblocking an occluded blood vessel 2 of the cardiovascular system (not shown) which has been occluded by an occlusion 3 formed by toughened hardened tissue which has become calcified and hardened into a hard plaque. The device 1 comprises a first elongated member, namely, an elongated catheter 5 extending from a proximal end 7 to a distal end 8, which terminates in a leading portion 9 for locating in the vessel 2 adjacent the occlusion 3. A bore 10 extends longitudinally through the catheter 5 and through the leading portion 9 for accommodating a second elongated member, namely, a guide wire 12 which also extends from a proximal end 14 to a distal end 15. The distal end 15 of the guide wire 12 terminates in a leading portion 17 which in turn terminates in a pointed distal tip 18 for penetrating through the occlusion 3 as will be described below. The proximal end 14 of the guide wire 12 terminates in a cylindrical handle 16, see FIG. 2, for facilitating rotating of the guide wire 12 in the bore 10 of the catheter 5 as will be described below.

An anchoring means comprising an inflatable balloon 19 is located adjacent the distal end 8 of the catheter 5 for anchoring the catheter 5 in the vessel 2. The catheter 5 extends through the balloon 19 so that the balloon 19 defines with the catheter 5 an annular hollow interior region 20. In this embodiment of the invention the catheter 5 is of double wall construction, having an inner wall 21 and an outer wall 22, which define therebetween an annular passageway 23 extending from the balloon 19 to the proximal end 7 for accommodating a suitable inflating medium, for example, an X-ray opaque dye solution therethrough to and from the hollow interior region 20 of the balloon 19 for inflating and deflating the balloon 19. Thus, when the catheter 5 is located in the vessel 2 with the leading portion 9 adjacent the occlusion 3, the balloon 19 is inflated for anchoring the catheter 5 with the leading portion 9 adjacent the occlusion 3 as illustrated in FIGS. 6 and 7. A coupling unit 24 at the proximal end 7 of the catheter 5 is provided for coupling the annular passageway 23 to a source (not shown) of the inflating medium for inflating the balloon 19.

The guide wire 12 and the catheter 5 co-operate with each other so that when the catheter 5 is anchored in the vessel 2 by the inflated balloon 19, the leading portion 17 of the guide wire 12 is urgeable off the leading portion 9 of the catheter 5 for urging the distal tip 18 of the guide wire 12 into engagement with the occlusion 3. In this embodiment of the invention the co-operating action between the guide wire 12 and the catheter 5 is achieved by providing an internal screw thread 25 in the bore 10 of the leading portion 9 of the catheter 5 which co-operates with a corresponding external screw thread 26 on the leading portion 17 of the guide wire 12. The co-operating action between the internal and external screw threads 25 and 26 results in rotation of the guide wire 12 in the appropriate angular direction being converted into linear motion of the guide wire 12 relative to the catheter 5 for urging the distal tip 18 of the guide wire 12 outwardly of the bore 10 and into engagement with the occlusion 3 for penetrating therethrough.

The guide wire 12 has a relatively high degree of torsional rigidity so that rotation of the proximal end 14 of the guide wire 12 is transferred into rotation of the distal end 15 of the guide wire 12.

In use, initially a standard soft tipped guide wire (not shown) is entered into the arterial network of the body through one of the femoral arteries and is urged through the arterial network into the arterial cardiovascular system until the leading distal portion of the standard guide wire is located in the occluded vessel 2 adjacent the occlusion 3. On the standard guide wire (not shown) with the distal tip thereof being located adjacent the occlusion 3, the catheter 5 of the device 1 is then advanced over the standard guide wire until its leading portion 9 is located in the vessel 2 adjacent and substantially abutting the occlusion 3. The balloon 19 is then inflated by a suitable inflating medium, for example, an X-ray opaque dye until the balloon 19 engages the inner periphery of the wall of the vessel 4 and the leading portion 9 of the catheter 5 is securely and centrally axially anchored in the vessel 4. The standard guide wire is withdrawn through the bore 10 of the catheter 5 and removed.

The guide wire 12 is then advanced through the bore 10 of the catheter 5 until the leading portion 17 of the guide wire 12 is located in the bore 10 adjacent the leading portion 9 of the catheter 5. At this stage the handle 16 of the guide wire 12 is gripped by hand and rotated for rotating the guide wire 12 in the appropriate direction about its longitudinal axis for engaging the external thread 26 of the leading portion 17 of the guide wire 12 with the internal thread 25 in the leading portion 9 of the catheter 5. Further rotation of the guide wire 12 advances the leading portion 17 of the guide wire 12 through the threaded portion of the bore 10, and in turn advances the distal tip 18 of the guide wire 12 into engagement with the occlusion 3. The guide wire 12 is rotated until the distal tip 18 has penetrated completely through the occlusion 3.

When the leading portion 17 of the guide wire 12 has been advanced completely through the occlusion 3, two options are available to stent the occlusion. Either the guide wire 12 may be left in place for guiding a balloon stent catheter (not shown) of the type which will be well known to those skilled in the art to the occlusion 3, or the guide wire 12 may be replaced by a standard guide wire (also not shown) for guiding a balloon stent catheter (not shown) to the occlusion 3. Should it be desired to use the guide wire 12 for guiding a balloon stent catheter (not shown) to the occlusion, the balloon 19 of the catheter 5 is deflated and the catheter 5 is removed. The balloon stent catheter (not shown) is then advanced over the guide wire 12, and the balloon with the stent located thereon is located in the occlusion 3. The balloon of the balloon stent catheter is then inflated, thereby urging the stent radially outwardly against the occlusion 3, and in turn dilating the occlusion 3. The balloon of the balloon stent catheter is then deflated, leaving the stent in place, which thereafter retains the occlusion in the dilated state with the vessel 2 unblocked and open. The balloon catheter with the deflated balloon and the guide wire 12 are removed.

Alternatively, should it be desired to use a standard guide wire (not shown) to guide the balloon stent catheter (not shown) to the occlusion 3, with the balloon 19 of the catheter 5 still inflated and anchoring the leading portion 9 of the catheter 5 in the vessel 2, the guide wire 12 is then withdrawn through the occlusion 3 until the external thread 26 on the leading portion 17 of the guide wire 12 engages the internal thread 25 of the bore 10 adjacent the leading portion 9 of the catheter 5. The handle 16 of the catheter 12 is then rotated in the appropriate direction for in turn rotating the leading portion 17 of the guide wire 12 relative to the leading portion 9 of the catheter 5 for urging the leading portion 17 of the guide wire 12 into and through the threaded bore 10 of the leading portion 9 of the catheter 5 until the external thread 26 on the leading portion 17 of the guide wire 12 has cleared the internal thread 26 on the leading portion 9. Thereafter the guide wire 12 is withdrawn from the catheter 5 by pulling the guide wire 12 through the bore 10 of the catheter 5.

On removal of the guide wire 12 from the catheter 5, a standard guide wire (not shown) is advanced through the bore 10 of the catheter 5 until the leading distal end of the standard guide wire passes across and through the occlusion 3. With the standard guide wire 5 so located in the occlusion 3, the balloon 19 of the catheter 5 is deflated and the catheter 5 is removed. The balloon stent catheter (not shown) is then advanced over the standard guide wire until the balloon with the stent located thereon is located in the occlusion 3. Thereafter the balloon of the balloon stent catheter is inflated as already described to urge the stent radially outwardly against the occlusion 3. With the stent in place in the occlusion 3, the balloon of the balloon stent catheter is deflated and the standard guide wire and the balloon catheter are then removed.

By replacing the guide wire 12 with a standard guide wire, a variety of tools may be advanced over the standard guide wire, such as stents, balloon catheters, laser catheters, arthrectomy catheters and other such catheters and devices.

A particularly important advantage of the invention is achieved by virtue of the fact that the leading portion 17 of the guide wire 12 is in screw thread engagement with the leading portion 9 of the catheter 5. Rotation of the guide wire 12 relative to the catheter 5 advances the leading portion 17 of the guide wire 12 through the occlusion 3. This, thus, gives a significant mechanical advantage over and above known methods where the leading portion of the guide wire is merely urged slidingly linearly through the bore of a catheter 5 for engaging and penetrating through an occlusion. In fact, the mechanical advantage achieved by the catheter and guide wire combination of the device 1 according to the invention is:

$$\pi \cdot D/p$$

where

D is the outer diameter of the handle 16 of the guide wire 12, and p is the pitch of the internal and external threads 25 and 26.

Accordingly, the larger the diameter of the handle 16, the greater will be the mechanical advantage, and similarly, by reducing the pitch of the threads, the mechanical advantage is likewise increased. Accordingly, by providing the guide wire 12 with the appropriate degree of torsional rigidity, the guide wire can be readily rotated by the handle 16 at the proximal end 14 thereof for, in turn, advancing the leading portion 17 of the guide wire 12 through the bore 10 of the leading portion 9 of the catheter 5 for penetrating the occlusion 3.

Another advantage of the device according to the invention is that it provides relatively fine pitch control to a user.

Referring now to FIG. 9, there is illustrated a portion of a device also according to the invention indicated generally by the reference numeral 30 also for unblocking an occluded vessel. The device 30 is substantially similar to the device 1 which has been described with reference to FIGS. 1 to 8, and similar components are identified by the same reference numerals. The only difference between the device 30 and the device 1 is in the anchoring means. In this embodiment of the invention the anchoring means comprises a balloon 19 formed by a plurality of interconnected annular segments 31. Otherwise, the device 30 is similar to the device 1 and its use is likewise similar to that of the device 1.

The advantage of the device 30 is achieved by virtue of the fact that the balloon 19 is formed by the annular segments 31. The provision of the balloon 19 in the form of annular segments 31 permits the catheter 5 adjacent its leading portion, when the annular segments 31 are inflated, to follow the curvature of an occluded vessel 2 if the vessel 2 is of curved configuration. By permitting the portion of the catheter 5 adjacent the leading portion 9 thereof to follow the curvature of the occluded vessel 2 permits the leading portion 9 of the catheter 5 to be centrally aligned with the occlusion, and in turn, the pointed distal tip 18 of the leading portion 17 of the guide wire 12 to be centred on the occlusion. Otherwise, if the occluded vessel were of curved configuration and the portion of the catheter 5 adjacent the leading portion 9 thereof did not follow the curvature of the vessel, the pointed distal tip 18 of the leading portion 17 of the guide wire 12 would not necessarily be centred on the occlusion when the leading portion 9 of the catheter 5 would be anchored in the vessel, and further advancing of the leading portion 17 of the guide wire 12 out of the bore 10 of the leading portion 9 could direct the pointed tip 18 of the leading portion 17 of the guide wire 12 through the wall of the vessel.

While the devices have been described for use for unblocking a vessel of an artery of the cardiovascular system, it will be readily apparent to those skilled in the art that the devices may be used for unblocking a vessel of any vascular system, whether arterial or venal. Needless to say, it will be appreciated that the devices may also be used for unblocking an occluded vessel in any other part of the body, for example, in the kidney, urinary tract or any other organ or vessel. Additionally, it is envisaged that the devices according to the invention and the method according to the invention may be used for unblocking an occlusion in any vessel, whether a biological vessel or a non-biological vessel, whether the vessel is in a human or animal body, or entirely unconnected with a human or animal body.

It is also envisaged that the devices and the methods according to the invention may be used for unblocking an occlusion in the gastrointestinal tract.

While the devices according to the invention have been described for unblocking a vessel, the devices according to the invention has many other uses, for example, the devices according to the invention may be used for remotely forming an opening or a bore in or through a medium or a membrane in a vessel, for example, for forming an opening in a membrane dividing a vessel or a membrane separating two vessels. However, in which case an appropriate anchoring means would be provided for anchoring the first member with the leading portion thereof adjacent the membrane at the location thereof through which the opening is to be formed. For example, if the devices were used to form an opening in a membrane or a wall of the heart which separates the heart into two or more vessels, the anchoring means would be appropriately provided for anchoring the first member with the leading portion thereof adjacent the membrane or wall of the heart at the location at which the opening is to be formed therethrough. Such an anchoring means may be provided by an appropriately sized and shaped balloon for engaging the walls of the vessel when inflated to facilitate anchoring of the first member with the leading portion thereof adjacent the membrane or wall. Further, the devices according to the invention may be used for drilling or forming a bore into tissue, such as muscle tissue of the heart for providing a blood supply to the muscle tissue.

Indeed, a further advantage of the devices according to the invention is their adaptability, and in particular, their adaptability for forming an opening or a bore in or through a medium, membrane or the like. Indeed, surgeons commonly wish to form a hole in the wall of the heart, for example, between chambers of the heart, and it is also not uncommon for surgeons to wish to create a communication between an artery or vein or other organs. These types of procedures are commonly carried out using a needle with a curved tip exiting a protecting catheter which is simply pushed through the catheter. By using the devices according to the invention for forming such a hole or creating such a communication, a safer and more controlled approach can be achieved, and such a safer, more controlled approach is readily achievable when the devices are provided with an externally threaded leading portion on the guide wire and an internally threaded bore in the leading portion of the catheter, since in which case the amount and rate of advance of the leading portion of the guide wire relative to the leading portion of the catheter can be finely controlled by controlling the angular rotation of the guide wire and the speed of rotation, as well as by appropriately selecting the thread pitch on the leading portion of the guide wire and in the bore of the leading portion of the catheter.

While the anchoring means has been described as comprising an annular balloon located adjacent the leading portion of the catheter, any other suitable anchoring means may be provided. Indeed, it will be readily apparent to those skilled in the art that a balloon of other shape and construction, which may or may not extend completely around the catheter, may be provided, and such a balloon typically would be shaped so that when inflated the balloon would define at least a portion of the interior of the vessel within which the catheter is to be anchored. Needless to say, the anchoring means may be provided at any other suitable location of the catheter besides adjacent the leading portion, and in certain cases, it is envisaged that the anchoring means may be provided remote of the leading portion.

While the co-operating action between the catheter and the guide wire has been described as being achieved by threading the leading portions of the guide wire and the catheter, other suitable co-operating means may be provided, which facilitates the leading portion of the guide wire to act against the leading portion of the catheter so that the guide wire can be urged off the catheter for penetrating the occlusion. It will also be appreciated that while the first member has been described as being provided by a catheter, any other suitable elongated member which terminates with a leading portion through which a bore extends may be used.

While the leading portion 17 of the guide wire 12 has been described as terminating in a pointed tip 18, the leading portion 17 may terminate in a tip of any other configuration, for example, the tip may be radiused, spade-edged, or the tip may be configured as a cutter, for example, with a serrated edge. Additionally, it is envisaged that the leading portion of the guide wire may terminate in a drill bit, or other suitable bit for boring or forming an opening or a bore in and through a medium, membrane, tissue, muscle tissue, occlusion or the like. Indeed, in certain cases, it is envisaged that the leading portion of the guide wire may terminate in a fluted drill bit.

It is envisaged that the internal threaded portion of the leading portion of the catheter may be provided as a separate element, which would be releasably secured to the leading portion of the catheter, and typically, would be releasably secured to the leading portion of the catheter adjacent the leading portion of the catheter extending from the distal portion of the inflatable balloon by, for example, a separate screw threaded arrangement, by a bayonet securing arrangement, or by any other suitable securing arrangement. Indeed, it is envisaged that where the threaded leading portion of the bore of the leading portion of the catheter is provided as a separate element, the said separate element would be internally threaded, and could form an internal sleeve extending into the bore 10 adjacent the leading end of the catheter.

The invention claimed is:

1. A device for unblocking an occluded vessel at a remote site having an occlusion therein, the device comprising:
   a first elongated member for passing through a lumen to the occluded vessel, the first member extending from a proximal end to a distal end and terminating in a distal leading portion adjacent the distal end thereof, and having an elongated bore extending longitudinally therethrough from the proximal end to the distal end and through the distal leading portion, the portion of the bore extending through the distal leading portion being internally threaded,
   an anchoring means located on the first member for anchoring the first member with the distal leading portion thereof adjacent the occlusion, and
   a second elongated member extending from a proximal end to a distal end and terminating in a distal leading portion, the distal leading portion of the second member terminating in a distal tip for urging through the occlusion for unblocking the occluded vessel, the distal leading portion of the second member being urgeable through the bore extending through the first member from the proximal end of the first member to the distal end and through the distal leading portion of the first member, and the distal leading portion of the second member being externally threaded, the external threads on the distal leading portion of the second member being engageable with the internal threads of the bore extending through the distal leading portion of the first member, so that rotation of the second member within the bore of the first member urges the distal leading portion of the second member off the anchored first member to in turn urge the distal tip of the second member into engagement with the occlusion when the first member is anchored by the anchoring means with the distal leading portion of the first member adjacent the occlusion.

2. A device as claimed in claim 1 in which the anchoring means is located adjacent the distal leading portion of the first member.

3. A device as claimed in claim 1 in which the anchoring means comprises an inflatable balloon located on the first member, and preferably the distal leading portion of the first member extending through the inflatable balloon so that the inflatable balloon defines with the distal leading portion of the first member an annular hollow interior region.

4. A device as claimed in claim 3 in which the inflatable balloon is remotely inflatable.

5. A device as claimed in claim 3 in which the first member comprises a communicating means for accommodating an inflating medium for remotely inflating the inflatable balloon.

6. A device as claimed in claim 1 in which the first member comprises an elongated catheter, and the second member comprises an elongated wire of torsional rigidity for transferring angular rotation of the second member adjacent the proximal end thereof into angular rotation adjacent the distal end thereof.

7. A device as claimed in claim 1 in which the anchoring means is adapted for engaging the wall of one of the occluded vessel and a vessel adjacent the occluded vessel for anchoring the distal leading portion of the first member adjacent the occlusion.

8. A device as claimed in claim 1 in which the device is adapted for unblocking an occluded vessel in a human or animal subject.

9. A method for unblocking an occluded vessel at a remote site having an occlusion therein, the method comprising:
urging a first elongated member through a lumen, the first elongated member extending from a proximal end to a distal end and terminating in a distal leading portion adjacent the distal end thereof and having an elongated bore extending longitudinally therethrough from the proximal end to the distal end and through the distal leading portion, the portion of the bore extending through the distal leading portion being internally threaded,
locating the distal leading portion of the first member adjacent the occlusion,
anchoring the first member by an anchoring means located on the first member with the leading portion of the first member adjacent the occlusion,
locating a distal leading portion of an elongated second member in the bore extending through the first member, the second elongated member extending from a proximal end to a distal end adjacent the distal leading portion of the second member, the distal leading portion of the second member being externally threaded and terminating in a distal tip,
urging the second member through the bore extending through the first member for urging the distal leading portion of the second member therethrough from the proximal end of the first member to the distal end thereof,
engaging the external threads of the distal leading portion of the second member with the internal threads of the distal leading portion of the first member,
rotating the second member within the bore of the first member so that the external threads of the distal leading portion of the second member co-operate with the internal threads of the distal leading portion of the first member for urging the second member off the anchored first member to urge the distal tip of the distal leading portion of the second member into engagement with the occlusion.

10. A method as claimed in claim 9 in which the first member is anchored by engaging the anchoring means with a wall of one of the occluded vessel and a vessel adjacent the occluded vessel.

11. A method as claimed in claim 9 in which the anchoring means comprises an inflatable balloon located on the first member, and the inflatable balloon is inflated for anchoring the first member with the distal leading portion thereof adjacent the occlusion.

12. A method as claimed in claim 11 in which the balloon is remotely inflated.

13. A method as claimed in claim 9 in which the first member is provided as a catheter, and the second member is provided as an elongated wire of torsional rigidity for transferring angular rotation of the second member adjacent the proximal end thereof into angular rotation adjacent the distal end thereof.

14. A method as claimed in claim 9 in which the method is adapted for unblocking an occluded vessel in a human or animal subject.

15. A method as claimed in claim 9 in which the first member with the second member engaged in the occlusion is withdrawn through the lumen, and a balloon stent catheter with a stent located on a balloon of the balloon stent catheter is passed through the lumen over the second member until the balloon with the stent thereon is located in the occlusion, and the balloon of the balloon stent catheter is inflated for dilating the occlusion.

16. A method as claimed in claim 15 in which the balloon of the balloon stent catheter is deflated and the balloon stent catheter and the second member are withdrawn through the lumen, leaving the stent in place in the occlusion.

17. A method as claimed in claim 9 in which the method is adapted for unblocking an occlusion in a blood vessel.

18. A device for remotely forming one of an opening and a bore through one of a medium within a vessel, a medium separating two vessels and a medium forming a vessel, the device comprising:
a first elongated member for passing through a lumen to the medium, the first member extending from a proximal end to a distal end and terminating in a distal leading portion adjacent the distal end thereof, and having an elongated bore extending longitudinally therethrough from the proximal end to the distal end and through the distal leading portion, the portion of the bore extending through the distal leading portion being internally threaded,
an anchoring means located on the first member for anchoring the first member with the distal leading portion thereof adjacent the medium, and
a second elongated member extending from a proximal end to a distal end and terminating in a distal leading portion, the distal leading portion of the second member terminating in a distal tip for urging through the medium to form the one of the opening and the bore therethrough, the distal leading portion of the second member being urgeable through the bore extending through the first member from the proximal end of the first member to the distal end and through the distal leading portion of the first member, and the distal leading portion of the second member being externally threaded, the external threads on the distal leading portion of the second member being engageable with the internal threads of the bore extending through the distal leading portion of the first member, so that rotation of the second member within the bore of the first member urges the distal leading portion of the second member off the anchored first member to in turn urge the distal tip of the second member into engagement with the medium when the first member is anchored by the anchoring means with the distal leading portion of the first member adjacent the medium.

19. A method for remotely forming one of an opening and a bore through one of a medium within a vessel, a medium separating two vessels and a medium forming a vessel, the method comprising:
urging a first elongated member through a lumen, the first elongated member extending from a proximal end to a distal end and terminating in a distal leading portion adjacent the distal end thereof and having an elongated bore extending longitudinally therethrough from the proximal end to the distal end and through the distal leading portion, the portion of the bore extending through the distal leading portion being internally threaded,
locating the distal leading portion of the first member adjacent the medium,
anchoring the first member by an anchoring means located on the first member with the distal leading portion of the first member adjacent the medium,
locating a distal leading portion of an elongated second member in the bore extending through the first member, the second elongated member extending from a proximal end to a distal end adjacent the distal leading portion of the second member, the distal leading portion of the second member being externally threaded and terminating in a distal tip, urging the second member through the bore extending through the first member for urging the distal leading portion of the second member therethrough from the proximal end of the first member to the distal end thereof, engaging the external threads of the distal leading portion of the second member with the internal threads of the distal leading portion of the first member, rotating the second member within the bore of the first member so that the external threads of the distal leading portion of the second member co-operate with the internal threads of the distal leading portion of the first member for urging the second member off the anchored first member to urge the distal tip of the distal leading portion of the second member into engagement with the membrane.

* * * * *

UNITED STATES PATENT AND TRADEMARK OFFICE
CERTIFICATE OF CORRECTION

PATENT NO. : 8,133,243 B2
APPLICATION NO. : 12/414077
DATED : March 13, 2012
INVENTOR(S) : Henry William Lupton et al.

It is certified that error appears in the above-identified patent and that said Letters Patent is hereby corrected as shown below:

In the Claims:

Column 10, line 45, claim 3: Delete "and preferably"

Signed and Sealed this
Fourteenth Day of May, 2013

Teresa Stanek Rea
*Acting Director of the United States Patent and Trademark Office*